United States Patent [19]
Sak

[11] Patent Number: 5,382,235
[45] Date of Patent: Jan. 17, 1995

[54] DEVICE FOR CAPTURING AND RETRACTING THE NEEDLE CANNULA OF A DISPOSABLE SYRINGE

[75] Inventor: Robert F. Sak, Boca Raton, Fla.

[73] Assignee: R.M.S. Safety, Inc., Boca Raton, Fla.

[21] Appl. No.: 175,236

[22] Filed: Dec. 29, 1993

Related U.S. Application Data

[63] Continuation-in-part of Ser. No. 101,723, Aug. 4, 1993, and a continuation-in-part of Ser. No. 129,312, Sep. 30, 1993, and a continuation-in-part of Ser. No. 86,988, Jul. 7, 1993, abandoned, and a continuation-in-part of Ser. No. 96,445, Jul. 26, 1993, abandoned.

[51] Int. Cl.⁶ .................. A61M 5/00; A61M 5/32
[52] U.S. Cl. ..................... 604/110; 604/195
[58] Field of Search ........ 604/110, 195, 196, 208–210, 604/225, 263; 128/919

[56] References Cited

U.S. PATENT DOCUMENTS

| | | | |
|---|---|---|---|
| 2,002,024 | 5/1935 | Wood | 604/225 |
| 4,026,287 | 5/1977 | Haller . | |
| 4,245,654 | 1/1981 | Raitto | 604/225 |
| 4,466,426 | 8/1984 | Blackman | 604/210 |
| 4,804,370 | 2/1989 | Haber et al. | 604/195 |
| 4,808,169 | 2/1989 | Haber et al. . | |
| 4,813,936 | 3/1989 | Schroeder . | |
| 4,838,870 | 6/1989 | Haber et al. . | |
| 4,950,241 | 8/1990 | Ranford . | |
| 4,995,870 | 2/1991 | Baskas . | |
| 5,047,016 | 9/1991 | Dolgin et al. . | |
| 5,188,597 | 2/1993 | Sweeney et al. . | |
| 5,221,262 | 6/1993 | Kite | 604/110 |
| 5,221,262 | 6/1993 | Kite . | |
| 5,290,233 | 3/1994 | Campbell | 604/195 |

Primary Examiner—C. Fred Rosenbaum
Assistant Examiner—Frank Wilkens, III
Attorney, Agent, or Firm—Banner, Birch, McKie & Beckett

[57] ABSTRACT

Existing syringes are retrofittable with structure for capturing and enabling retraction of so-called extended needles proximally into the cylinders of the syringes upon complete expulsion of a medicament, without requiring alteration of the existing structure for attaching pistons and piston stems in order to mount the capturer. At complete expulsion of fluid from the cylinder, the typical rubber piston is pierced by a sharp proximal end of the needle. Flexible tabs of the capturer deflect proximally while maintaining engagement with the intruding needle, in order to cooperate with particular structure of the needle so as to maintain the captured state. The modification of the extended needle cannula also may include providing side ports which serve the dual functions of ensuring complete expulsion of the medicament and of cooperating with tabs of the capturer so as to cause canting of the retracted needle. Other or further modification of the needle may include a cone-shaped deflector for deflecting the capturer tabs proximally during capture and for preventing disengagement of the captured needle. An audible indicator provides the user with an indication that the needle is captured or, alternatively, that the piston has traveled distally sufficiently to effect the capture.

19 Claims, 6 Drawing Sheets

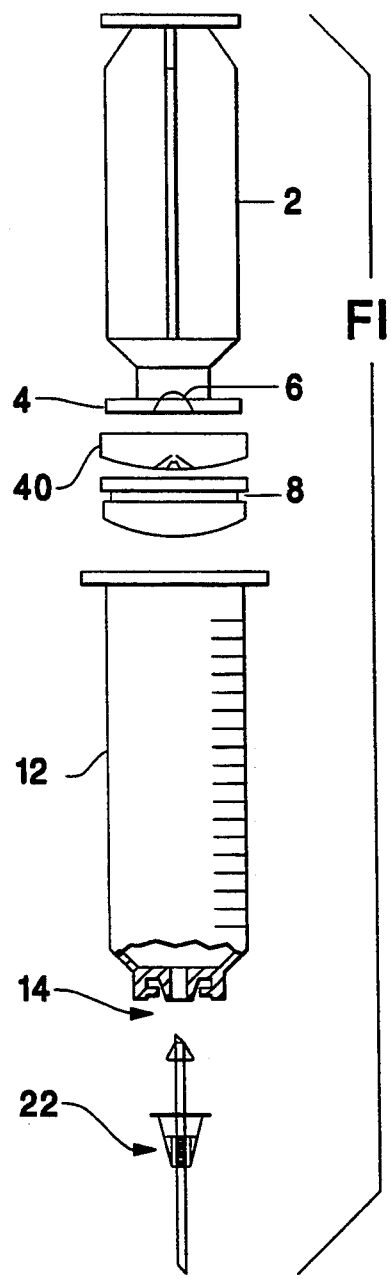
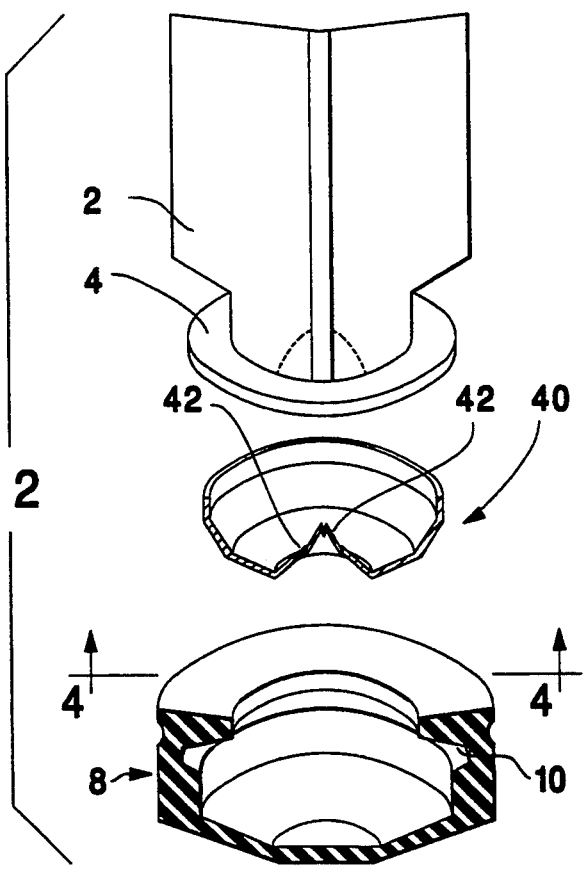
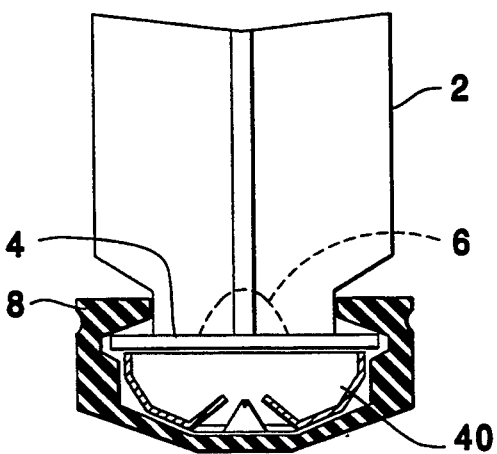
FIG. 1
FIG. 2
FIG. 3

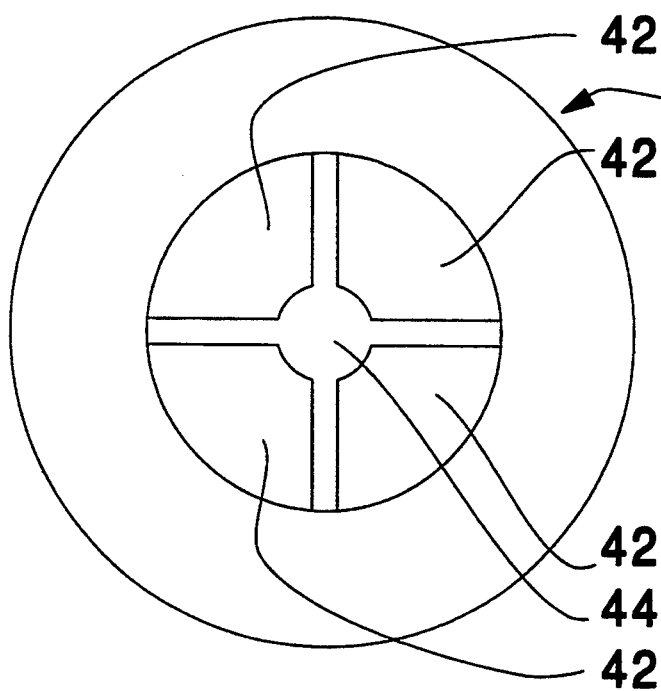
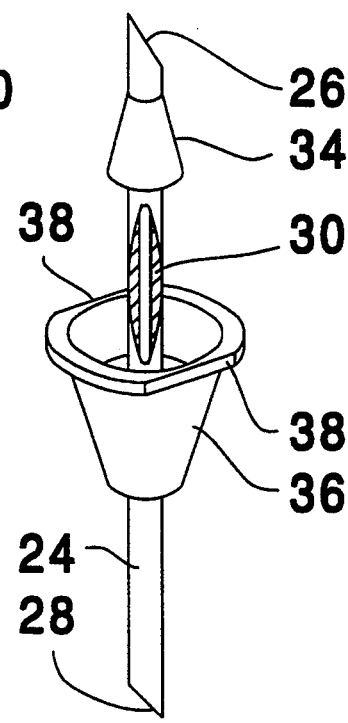
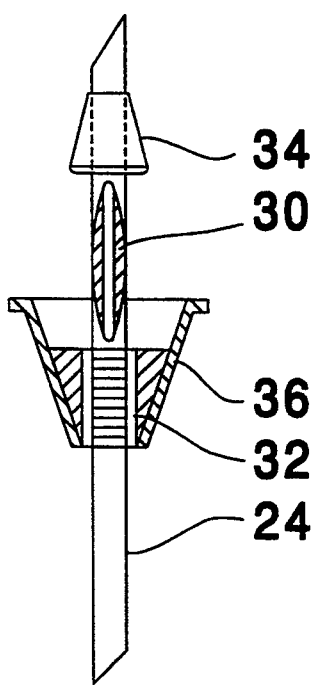
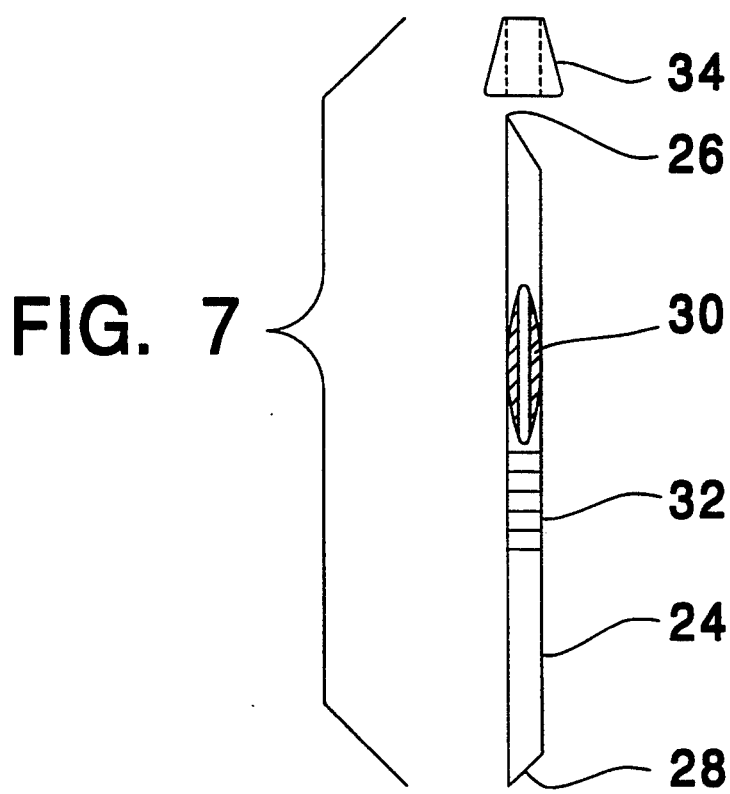
FIG. 4
FIG. 6
FIG. 5
FIG. 7

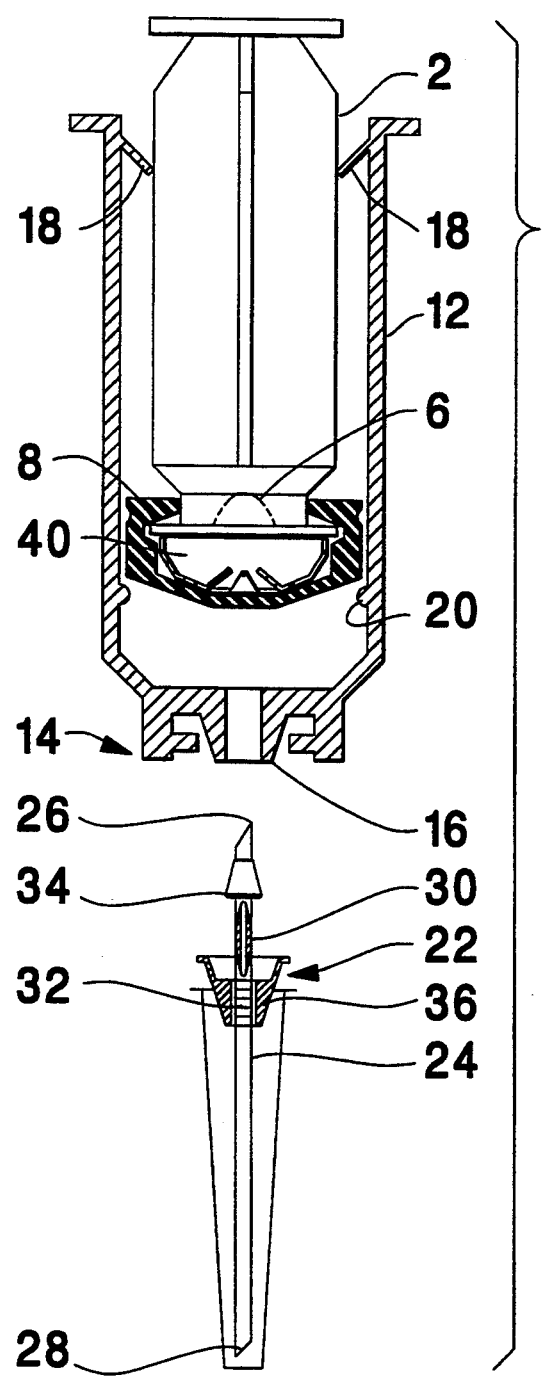
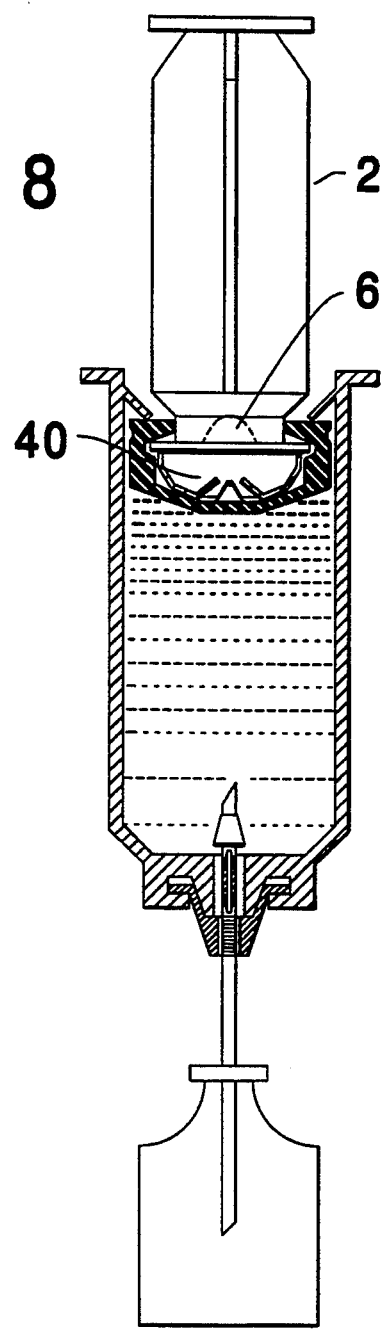

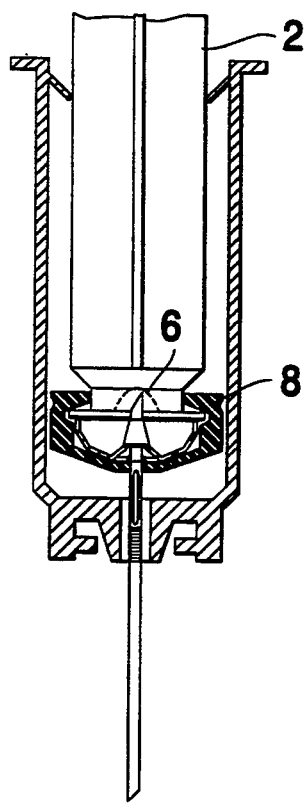
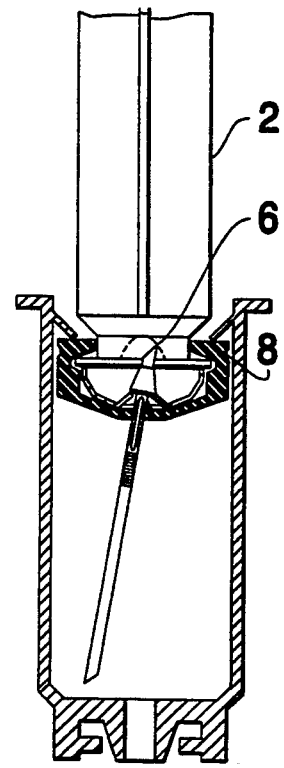
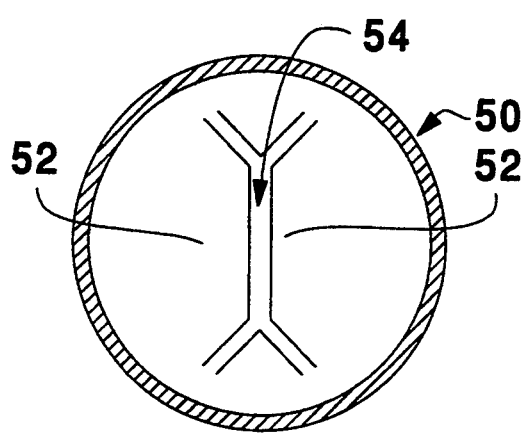
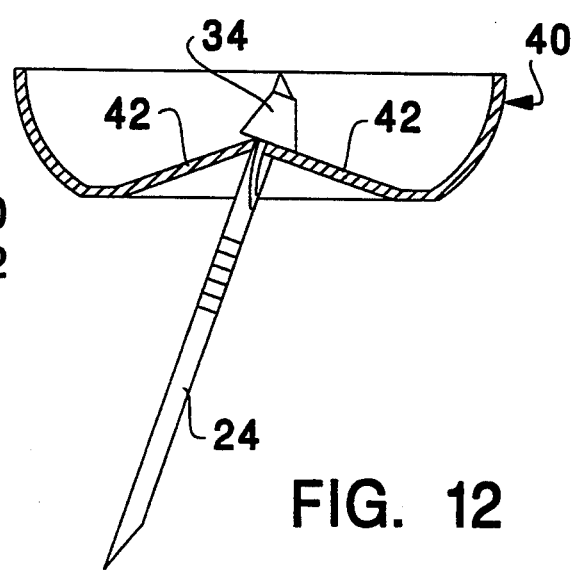

DEVICE FOR CAPTURING AND RETRACTING THE NEEDLE CANNULA OF A DISPOSABLE SYRINGE

CROSS REFERENCES TO CONTINUING APPLICATIONS

This application is a continuation-in-part of 08/101,723 filed Aug. 4, 1992 pending, and a continuation-in-part of 08/129,312 filed Sep. 30, 1993 pending, and a continuation-in-part of 08/086,988 filed Jul. 7, 1993 abandoned, and a continuation-in-part of 08/096,445 filed Jul. 26, 1993 abandoned.

PRIOR ART CROSS-REFERENCES

U.S. Pat. No. 4,026,287 to Haller, entitled Syringe with Retractable Cannula, dated May 31, 1977.

U.S. Pat. No. 4,804,370 to Haber et al., entitled Disease Control Syringe Having a Retractable Needle, dated Feb. 14, 1989.

U.S. Pat. No. 4,808,169 to Haber et al., entitled Disposable Safety Syringe Having Means for Retracting its Needle Cannula into its Medication Cartridge, dated Feb. 28, 1989.

U.S. Pat. No. 4,813,936 to Schroeder, entitled Retracting Hypodermic Needle, dated Mar. 21, 1989.

U.S. Pat. No. 4,838,870 to Haber et al., entitled Removable Needle Attachment Having a Detachable Needle, dated Jun. 13, 1989.

U.S. Pat. No. 4,950,241 to Ranford, entitled Disposable Syringe, dated Aug. 21, 1990.

U.S. Pat. No. 4,995,870 to Baskas, entitled Disposable Syringe with Retractable Needle, dated Feb. 26, 1991.

U.S. Pat. No. 5,047,016 to Dolgin et al., entitled Fluid Passing Apparatus with Means for Covering the Same, dated Sep. 10, 1991.

U.S. Pat. No. 5,188,597 to Sweeney et al., entitled Safety Needle Syringe, dated Feb. 23, 1993.

U.S. Pat. No. 5,221,262 to Kite, entitled Hypodermic Needle Retractor, dated Jun. 22, 1993.

The disclosures of the above patents are expressly incorporated herein by reference.

BACKGROUND OF THE INVENTION

The invention is in the field of disposable hypodermic syringes for injecting medication into patients. In particular, the invention is directed to a simplified, economical means of adapting existing syringes to capture the needle cannula and retrieve it into the cylinder of the syringe in a safe manner after expulsion of medicament.

Disposable hypodermic syringes are routinely used to administer medication to patients, thus presenting the requirement for proper disposal of used and contaminated needles. In an emergency situation, this requirement sometimes is overlooked by the caregiver, whether for practical reasons or otherwise. Separate procedures for disposal are limited at best, consisting of (i) breaking the needle off in a special container which is separate from the syringe, or (ii) using special equipment to assemble or disassemble the syringe, both of which require extra steps for proper disposal of the contaminated device.

Even needles which are broken off still can present a hazard of so-called "needle strikes" to trash removal personnel. The potential for needle strikes to health caregivers and associated personnel can cause a high degree of anxiety and require expensive testing procedures of suspected needle strikes. More and more health care personnel are exposed to the risk of infection with the increasing care requirements of HIV- and AIDS-infected individuals, as well as the risk of hepatitis B and other infectious diseases.

Prior attempts to address safe disposal of contaminated needles by retracting the used needle into the cylinder of the syringe have required (i) redesign of the syringe, needle, and parts therein, and/or (ii) plural step disposal procedures which are not practical in emergency situations.

For instance, the above-referenced U.S. Pat. No. 4,995,870 discloses structure which requires loosening of the hub in order to release the needle from a plug and thus allow for withdrawal of the used needle into the cylinder of the syringe. While manipulating the hub to allow for the retraction, the caregiver must either expose his/her hand to the distal end of the used and possibly contaminated needle or use an auxiliary device for covering the tip of the used needle.

The needles of above-referenced U.S. Pat. Nos. 4,026,287; 4,804,370; and 5,221,262 all are integral with the syringe cylinder rather than being removably attachable assemblies and, thus, prevent adaptability to syringes having the so-called Luer lock connection or other types of removable attachments for non-integral needle assemblies.

Some prior art devices have so-called extended needles which protrude proximally into the syringe cylinder past their points of attachment to the needle assembly such that complete expulsion of fluid from a cylinder is negated. Since fluid is not compressible, any residual fluid in the distal end of the cylinder opposes further distal movement of the piston once the proximal opening of the needle is blocked by the piston or otherwise. Under this condition, further distal movement of the piston and capturing of the extended needle for retraction is rendered non-functional or, at best, difficult.

Some prior art devices also provide for a barbed, proximal end of the extended needle be impaled in a full (as opposed to hollow) piston or the like to effect capture and retraction, thus requiring more force to effect the capture.

The needle capturers of the prior art are integral with the corresponding piston stems and, thus, do not present structure which lends it self to retrofitting to existing piston stems of particular syringes which are widely used in the industry.

Thus, it is an object of the invention to provide means for converting most non-retracting hypodermic syringes currently on the market to retractable safety syringes, with only minor, non-disruptive changes in the manufacturing process.

Further, it is an object of the invention to provide a separately attachable capturing device for retrofitting to a syringe without altering the structure of an already existing means for attaching the rubber piston to the piston stem.

Still further, it is an object of the invention to provide an add-on needle capturer which is receivable in the existing rubber piston of a syringe and at least partially retained therein by the existing means of attaching the rubber piston to the end of the stem.

Also, it is an object of the invention to modify or replace existing needles, with so-called extended needles having side ports so as to provide for complete expulsion of fluid from the cylinder and capture of the needle without difficulty, in a manner which also provides for canting of the retracted needle.

Additionally, it is an object of the invention to provide an audible indicator which, in one form, signals the actual capture of the needle and, in another form, signals that the piston has displaced sufficiently distally for capture of the needle to have taken place.

These and other objects will become more apparent from a detailed study of the remaining disclosure.

BRIEF SUMMARY OF THE INVENTION

Existing syringes are retrofittable with structure for capturing and enabling retraction of so-called extended needles proximally into the cylinders of the syringes upon complete expulsion of a medicament, without requiring alteration of the existing structure for attaching pistons and piston stems in order to mount the capturer. At complete expulsion of fluid from the cylinder, the typical rubber piston is pierced by a sharp proximal end of the needle. Flexible tabs of the capturer deflect proximally while maintaining engagement with the intruding needle, in order to cooperate with particular structure of the needle so as to maintain the captured state. The modification of the extended needle cannula also may include providing side ports which serve the dual functions of ensuring complete expulsion of the medicament and of cooperating with tabs of the capturer so as to cause canting of the retracted needle. Other or further modification of the needle may include a cone-shaped deflector for deflecting the capturer tabs proximally during capture and for preventing disengagement of the captured needle. An audible indicator provides the user with an indication that the needle is captured or, alternatively, that the piston has traveled distally sufficiently to effect the capture.

BRIEF DESCRIPTION OF THE DRAWINGS

FIG. 1 is an exploded view, partially in cross-section, of a popular disposable syringe modified by incorporation of the invention so as to provide for safe capturing and retracting of the needle cannula.

FIG. 2 is an enlargement of a portion of FIG. 1.

FIG. 3 is similar to FIG. 2, but with the component parts thereof assembled.

FIG. 4 is plan view of the novel needle capturer.

FIG. 5 is an elevational view, partially in cross-section of the needle assembly without the protective cover thereon.

FIG. 6 is an isometric view of the needle assembly of FIG. 5, for illustrating one type of removable connection means.

FIG. 7 is an exploded elevational view illustrating the needle cannula and a deflector of the needle assembly.

FIGS. 8–11 are schematics for illustrating the procedure for using the invention.

FIG. 12 is an enlarged, partially sectioned view of a portion of FIG. 11.

FIG. 13 is a plan view of the concave side of the capturer and illustrating an alternate embodiment of the tab structure thereof.

DETAILED DESCRIPTION OF THE INVENTION

Figure 14:
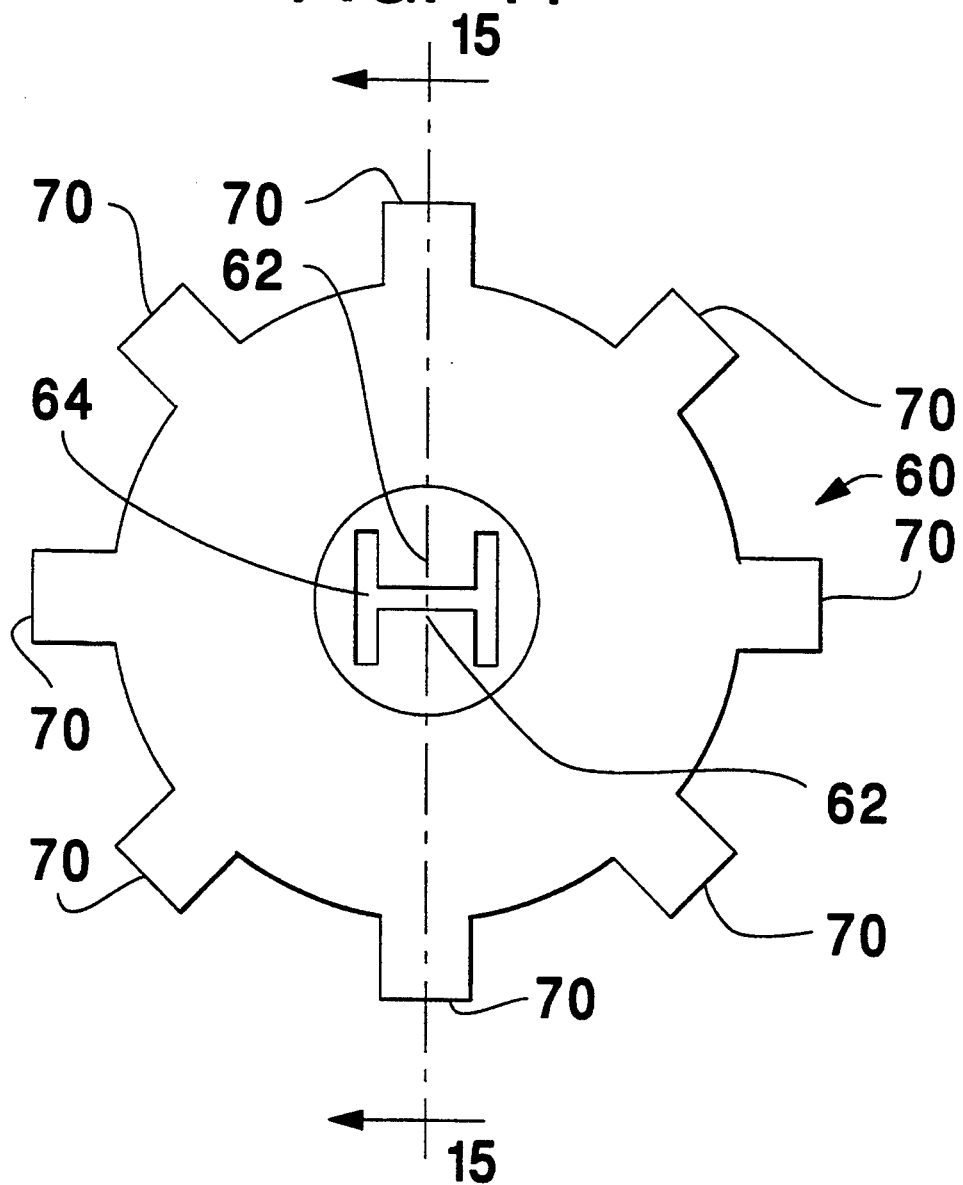
FIG. 14 is a bottom plan view of an alternate structure for the capturer.
Figure 15:
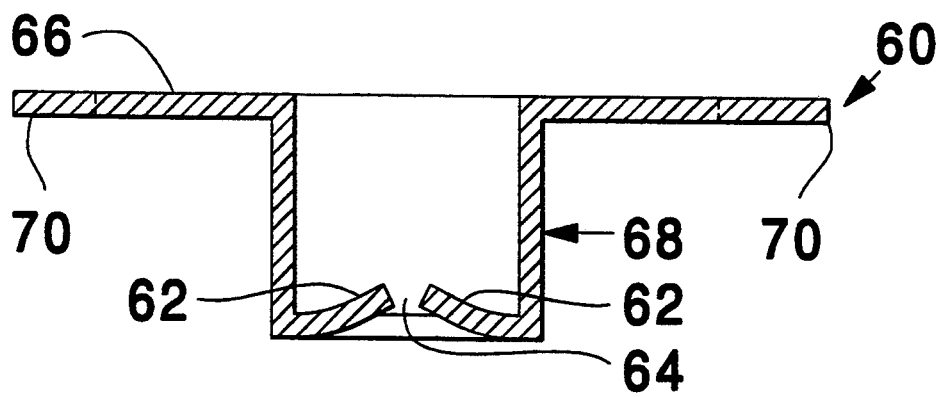
FIG. 15 is a cross-section, as view generally in the direction of arrows 15—15 of FIG. 14.
Figure 16:
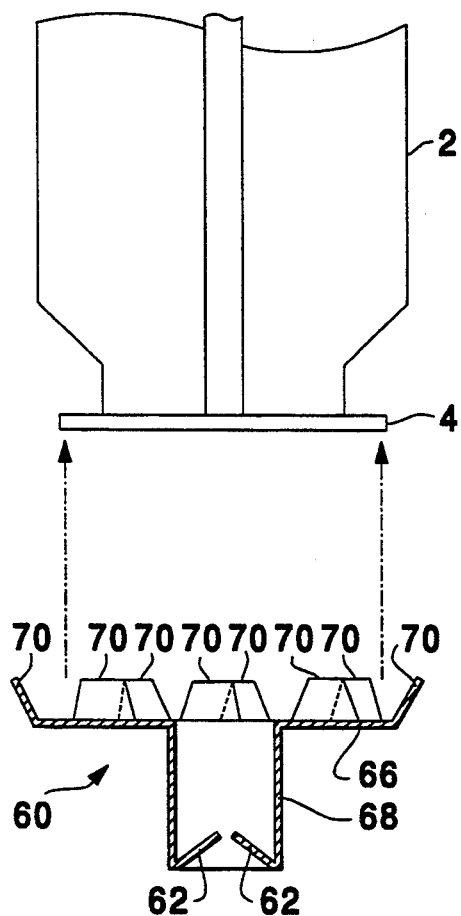
FIGS. 16 and 17 are somewhat schematic views illustrating attachment of this alternate capturer to the distal end of the piston stem of a syringe which is widely used in the industry.
Figure 17:
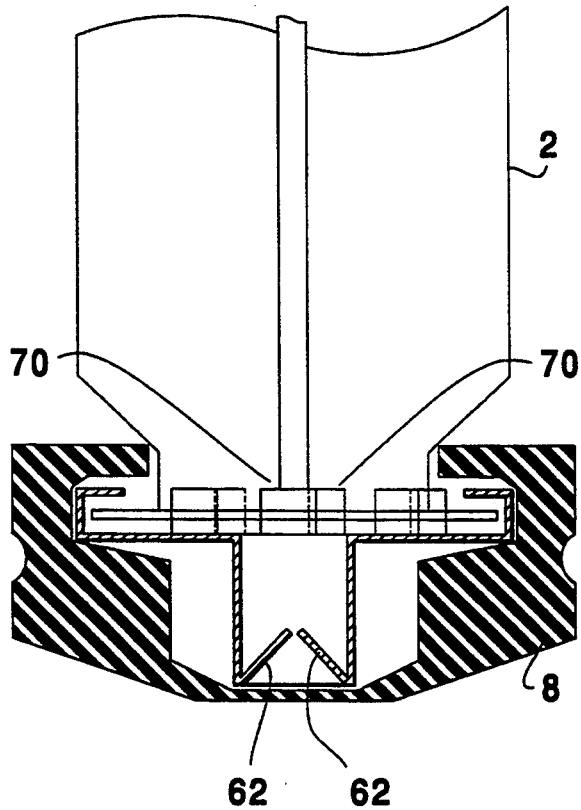

Referring to the Figures for an understanding of the invention, an elongated piston stem 2 of the typical syringe has a distal end flange 4 which is engageable within groove 10 of generally hollow rubber piston 8. In one embodiment of the invention, a capturer 40 is receivable within the hollow portion of rubber piston 8 and retained therein by completion of the attachment of the piston 8 to the flange 4, as best seen in FIGS. 2 and 3. The integrity of the connection between flange 4 and groove 10 is ensured by the pressure between the circumferential surface of piston 8 and the internal surface of cylinder 12. It is preferred that the capturer 40 is retained in a snug fitting relationship within the concavity of piston 8, as illustrated herein.

The typical syringe also includes a cylinder 12 to the distal end of which a separate needle assembly is removably attachable. The point of attachment typically is provided with a Luer lock-type of connection which is well known to those skilled in the art. Alternatively, other connectors may be provided for removably attaching the needle assembly.

Referring to FIGS. 5 and 6, a needle assembly is illustrated as comprising the typical cannula 24 which is modified to have at least one lateral port 30 and a conically shaped deflector member 34 attachable thereto in a generally permanent manner. Cannula 24 also has grooves 32 to aid in attachment of the Luer lock-type hub 36 onto the cannula 24 by means of an adhesive. Preferably, this adhesive has a release factor of two pounds pressure. The distal end of cannula 24 is pointed for insertion into the patient and the proximal end thereof is sharpened for piercing of the rubber piston 8 upon complete expulsion of the fluid contained in cylinder 12. In order to ensure uninterrupted and complete expulsion of fluid from cylinder 12, the so-called extended needle cannula 24 is provided with one or more of the lateral ports 30 for evacuation of any fluid remaining upon the proximal end of cannula 24 becoming blocked by the piston 8 or associated structure at the distal end of stem 2.

FIG. 4 illustrates a capturer 40 having flexible tabs 42 for capturing the needle cannula 24 therein in order to effect subsequent retraction of the needle into cylinder 12. The tips of the free ends of tabs 42 nave been removed so as to define the axial opening 44 through which the deflector 34 may pass more easily into capturer 40 while deflecting the free ends of flexible tabs 42 proximally.

In use of the invention, the novel capturer 40 is installed within the concavity of typical piston 8 and retained securely therein by mating flange 4 of the typical stem 2 in piston groove 10 during packaging of the syringe. The packaged syringe has stem 2 telescoped into cylinder 12 far enough for piston 8 to engage a ridge 20 (FIG. 8) protruding inwardly from the internal surface of cylinder 12. Ridge 20 functions to indicate the extent to which stem 2 can be telescoped without causing a subsequently attached needle assembly to be captured as soon as it is attached to the distal end of the springe. In addition to providing tactile feedback of such a limit to the user, it is contemplated that movement of the piston 8 across ridge 20 can provide an audible noise such as a "click" to indicate the occurrence of sufficient distal displacement of the piston 8 for capturing the extended needle cannula 24.

A needle assembly preferably would be packaged with the standard sterility shield 22 (one-half of which is illustrated in FIG. 8) for safe handling of the needle assembly during attachment thereof to the distal end of cylinder 12.

Deflector 34 is sized to pass through the aperture provided on existing syringes of all sizes. Once the user installs the needle assembly on the syringe in the usual manner of attachment, the protection shield 22 is removed from the cannula 24 for infusing a fluid medicament into the cylinder 12 as illustrated in FIG. 9. The extent of withdrawal of stem 2 from cylinder 12 during such infusion is limited by tabs 18 engaging the proximal end of piston 8. FIG. 10 illustrates the condition of the syringe upon complete expulsion of medicament therefrom, with pointed proximal end 26 of the cannula 24 having pierced the rubber of piston 8 and passed between the flexible tabs 42 to effect capture of the needle cannula 24. As seen in FIG. 10, it is sometimes necessary to provide a concavity 6 or the like in the distal end of stem 2 so as to ensure sufficient passage of the deflector 34 into capturer 40 such that flexible tabs 42 can engage that portion of cannula 24 which is distal of deflector 34.

In a preferred embodiment, complete passage of deflector 34 past the tips of tabs 42 would result in a series of audible clicks to alert the user that the safety mechanism has been fully engaged. Although not shown in the drawings, the tips of flexible tabs 42 may be staggered axially of the syringe in order to provide such a series of clicks and to ensure canting of the needle cannula 24 to the position illustrated in FIGS. 11 and 12. In achieving the retracted state of FIG. 11, the needle cannula 24 is pulled free of the adhesive seal between the grooves 32 and hub 36.

Canting of the needle cannula 24 also is facilitated by engagement of a lateral port 30 with at least one of the flexible tabs 42, as illustrated in FIG. 12.

It also is contemplated that the deflector member 34 may be omitted from the needle assembly of FIG. 5. In such case, capturer 50 of FIG. 13 is provided with the alternate shaped opening 54 between flexible tabs 52 in order to closely grip the deflectorless needle 24 in the region of the lateral openings 30. Machining of lateral ports 30 results in a reduction in circumference of the needle 24 so as to facilitate capturing of the needle by tabs 52. It is preferred that the slit opening 54 between tabs 52 be half the diameter of the needle cannula. It also is contemplated that the opening between flexible tabs 52 may be situated off-center of the capturer 50, such as would be provided by tabs 52 being of different lengths, in order to ensure canting of the needle.

Figure 18:
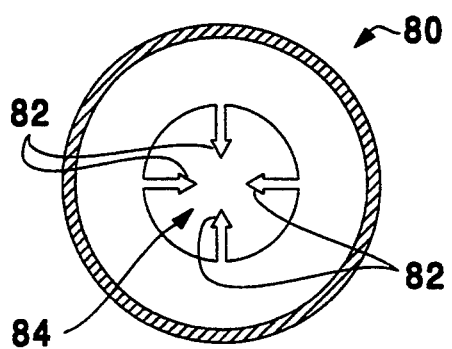
FIG. 18 is a view similar to that of FIG. 13 and illustrating another embodiment of tab structure for the capturer.

FIG. 18 illustrates capturer 80 with sill another structure for the needle retaining tabs. In this embodiment, the tabs 82 are shaped like arrow-heads and sized so that an arrow tip can protrude into a lateral port 30 of cannula 24 and, thus, facilitate a more secure capture of the cannula needle 24 for retraction into cylinder 12. Canting or the needle is also facilitated by this structure. FIG. 18 illustrates an entrance gap 84 which is ample enough to easily pass the deflector 34, but may be smaller when used with deflectorless needles.

The reduction in diameter of the needle 24 in the region of the lateral port 30 also provides a weak point for causing the needle to bend and break if an attempt is made to reexpose the canted needle through the distal tip of the syringe.

An alternate capturer 60 is illustrated in FIGS. 14 and. 15 as having a generally flat, closed, proximal portion 66 from which attachment fingers 70 radiate and a cylindrical member 68 protrudes axially. Alternatively, member 68 could be open at both ends. Member 68 thus defines a receptacle within which the needle is captured by flexible locking tabs 62 in a manner similar to the locking tabs 52 of FIG. 13. The radial fingers 70 provide for attachment of the capturer 60 to the flange 4 of stem 2 prior to fitting piston 8 thereupon. It is to be noted that the subsequently attached piston 8 supplements and retains attachment of fingers 70 onto flange 4. As with the other embodiments, the opening 64 of capturer 60 also may be sized and/or shaped to facilitate capturing of cannulas with deflectors such as deflector 34.

Thus, it will be seen that the objects set forth above, among those made apparent from the preceding description, are efficiently attained and, since certain changes may be made in the construction set forth without departing from the scope of the invention, it is intended that all matter contained in the above description or shown in the accompanying drawings shall be interpreted as illustrative and not in a limiting sense. For instance, although the invention has been described with respect to removably attachable needle assemblies, it is also contemplated that similar adaptations may be made to those needle assemblies which are affixed to be integral with the syringe.

It is to be understood also that the following claims are intended to cover all of the generic and specific features of the invention herein described, and all statements of the scope of the invention which, as a matter of language, might be said to fall therebetween.

Now that the invention has been described, I claim:

1. In a syringe having a cylinder, and needle extending into said cylinder, and a piston stem with a flange on a distal end thereof, said flange supporting a piston for axial displacement within said cylinder, and said piston presenting a concavity facing proximally of said syringe and a groove in an internal surface of said concavity, said groove being engaged by said flange to facilitate attachment of said piston to said stem while leaving a void generally defined by said stem distal end and said internal surface of said concavity, the improvement comprising:

means for enabling a proximal end of said needle to pierce said rubber piston upon generally complete expulsion of fluid from said cylinder; and means for receiving and capturing said needle proximal end after piercing of said rubber piston, said capturing means comprising a separate, generally hollow device received within said void and at least partially retained therein by said piston attached to said stem, such that said capturing means is adapted to existing syringes without modification of said piston and stem.

2. The improvement as in claim 1, and further comprising:

flexible tab means, on a distal end of said capturing means, for flexing toward an open state in a proximal direction during entry of said needle into said capturing means and back toward a closed state to effect capturing of said needle.

3. The improvement as in claim 1, and said capturing means further comprising:

generally radially protruding finger means for wrapping around said flange to effect attachment of said capturing means to said distal end of said stem; and
said groove covering and supplementing said finger means attachment of said capturing means to said distal end of said stem.

4. The improvement as in claim 2, and further comprising:
means for canting said needle when retracted into said cylinder, said canting means comprising free ends of at least two tabs of said tab means being displaced axially from each other.

5. The improvement as in claim 2, and further comprising:
means for canting said needle when retracted into said cylinder, said canting means comprising means for modifying an existing extended needle with structure which is engaged by said tab means to effect said canting.

6. The improvement as in claim 5, wherein said modifying means comprises:
at least one lateral aperture providing for fluid passage laterally from an axial bore of said needle, said aperture being engaged with said tab means in order to provide for said canting.

7. The improvement as in claim 2, and said needle further comprising:
at least one lateral aperture providing for fluid passage laterally from an axial bore of said needle, said aperture being engaged with said tab means in order to effect said capturing.

8. The improvement as in claim 7, and further comprising:
a generally cone-shaped deflector means, attached to an existing needle, for deflecting and cooperating with said tab means in order to retain said capture of said needle.

9. The improvement as in claim 2, and further comprising:
audible means for indicating the capturing of said needle upon generally complete expulsion of fluid from said syringe.

10. The improvement as in claim 9, where in said audible indicating means comprises:
means for producing a distinctive click upon displacing a tip of at least one of a plurality of tabs of said tab means during capturing of a needle.

11. The improvement as in claim 10, and further comprising: means for producing a series of distinctive clicks corresponding to displacing of tips of a series of said tabs.

12. The improvement as in claim 1, and further comprising:
audible signal means for indicating a particular amount of displacement of said piston distally within said cylinder.

13. The improvement as in claim 12, wherein said audible signal means comprises a ridge protruding from an inner surface of said cylinder and engaged by said piston generally as said needle pierces said piston.

14. The improvement as in claim 1, and further comprising a ridge protruding radially inward from an inner surface of said cylinder, said ridge providing limited resistance to distal movement of said piston in order to indicate a limit of distal movement of said piston past which said capturing occurs.

15. The improvement as in claim 7, and each tab of said tab means further comprising:
a pointed end means for protruding into a corresponding said lateral- aperture, 16. The improvement as in claim 12, wherein said audible signal means comprises:
said flexible tabs interacting with structure of said needle during said capture.

17. The improvement as in claim 16, and further comprising:
tips of said flexible tabs being spaced axially apart so as to generate a series of clicks during interacting with said needle during said capture.

18. An apparatus by which the proximal end of an extended needle is captured in order to enable reaction of said needle into a cylinder of a syringe having a piston stem with a flange at a distal end thereof and a piston presenting a concavity facing proximally of said syringe and a groove in an internal surface of said concavity, said groove being engaged by said flange to facilitate attachment of said piston to said stem while leaving a void generally defined by said stem distal end and said internal surface of said concavity, said apparatus comprising:
means for enabling a proximal end of said needle to pierce said rubber piston upon generally complete expulsion of fluid from said cylinder; and
means for receiving and capturing said needle proximal end after piercing of said rubber piston, said capturing means comprising a separate, generally hollow device received within said void and having generally radially protruding finger means for wrapping around said flange to effect attachment of said capturing means to said distal end of said stem and being at least partially retained therein by said piston attached to said stem with said groove covering and supplementing said finger means attachment of said capturing means to said distal end of said stem, such that said capturing means is adapted to existing syringes without modification of said piston and stem.

19. An apparatus by which the proximal end of an extended needle is capturable in order to enable retraction of said needle into a cylinder of a syringe having a piston stem with a flange at a distal end thereof and a piston presenting a concavity facing proximally of said syringe and a groove in an internal surface of said concavity, said groove being engaged by said flange to facilitate attachment of said piston to said stem while leaving a void generally defined by said stem distal end and said internal surface of said concavity, said apparatus comprising:
means for enabling a proximal end of said needle to pierce said rubber piston upon generally complete expulsion of fluid from said cylinder; and
means for receiving and capturing said needle proximal end after piercing of said rubber piston, said capturing means comprising a separate, generally hollow device received within said void and at least partially retained therein by said piston attached to said stem, such that said capturing means is adapted to existing syringes without modification of said piston and stem;
at least one lateral aperture providing for fluid passage laterally from an axial bore of said needle;
flexible tab means, on a distal end of said capturing means, for flexing toward an open state in a proximal direction during entry of said needle into said capturing means and back toward a closed state to effect capturing of said needle, and comprising at least two tabs and each said tab having a pointed end means for protruding into and engaging a corresponding said lateral aperture in order to effect said capturing.

* * * * *